United States Patent [19]
Stroebel et al.

[11] Patent Number: 5,674,257
[45] Date of Patent: Oct. 7, 1997

[54] PACEMAKER ADAPTED TO PREFER UNDERLYING SINUS RHYTHM OVER OTHER RATE RESPONSIVE INDICATOR

[75] Inventors: John C. Stroebel, Blaine; H. Toby Markowitz, Roseville, both of Minn.

[73] Assignee: Medtronic, Inc., Minneapolis, Minn.

[21] Appl. No.: 611,357

[22] Filed: Mar. 5, 1996

Related U.S. Application Data

[60] Division of Ser. No. 343,166, Nov. 22, 1994, Pat. No. 5,522,859, which is a continuation-in-part of Ser. No. 129,631, Sep. 29, 1993, abandoned.

[51] Int. Cl.$^6$ .................................................. A61N 1/365
[52] U.S. Cl. ............................................................ 607/17
[58] Field of Search .......................................... 607/9, 17

[56] References Cited

U.S. PATENT DOCUMENTS

| | | | |
|---|---|---|---|
| 3,857,399 | 12/1974 | Zacouto | 607/9 |
| 3,921,642 | 11/1975 | Preston et al. | 607/9 |
| 4,257,423 | 3/1981 | McDonald et al. | 128/419 |
| 4,312,355 | 1/1982 | Funke | 128/419 |
| 4,374,382 | 2/1983 | Markowitz | 340/870.01 |
| 4,428,378 | 1/1984 | Anderson et al. | 128/419 |
| 4,556,063 | 12/1985 | Thompson et al. | 128/419 |
| 4,856,523 | 8/1989 | Sholder et al. | 128/419 |
| 4,951,667 | 8/1990 | Markowitz et al. | 128/419 |
| 5,074,304 | 12/1991 | Hedin et al. | 128/419 |
| 5,085,215 | 2/1992 | Nappholz et al. | 128/419 |
| 5,127,404 | 7/1992 | Wyborny et al. | 128/419 |
| 5,144,949 | 9/1992 | Olson | 128/419 |
| 5,154,170 | 10/1992 | Bennett et al. | 128/419 |
| 5,247,930 | 9/1993 | Begemann et al. | 607/11 |

*Primary Examiner*—William E. Kamm
*Attorney, Agent, or Firm*—Harold R. Patton; Michael B. Atlass

[57] ABSTRACT

A dual chamber, rate-responsive pacemaker for pacing a patient's heart novelly allows tracking of the patient's sinus rate when the sinus rate is slightly less than the sensor rate; i.e., within a predetermined "Sinus Preference Window Maximum Rate Drop." Pacing at the sensor rate occurs when the sensor rate exceeds the sinus rate by more than the Sinus Preference Window Maximum Rate Drop. In the preferred embodiment a Sinus Preference Window, which occurs at the end of the ventricle-to-atrium interval, is decremented with successive heart beats by a programmable delta to increase the pacing rate until the Sinus Preference Window reaches zero, in which case the pacemaker paces at the sensor rate. The Sinus Preference Window is reset to its maximum value upon either the detection of an atrial sensed event, or upon the expiration of a programmable Sinus Check Interval. The pacemaker paces at the sinus rate or the maximum rate drop rate, whichever is faster, for a number of recovery beats, and then increments the pacing rate up to the sensor rate.

6 Claims, 10 Drawing Sheets

PACEMAKER ADAPTED TO PREFER UNDERLYING SINUS RHYTHM OVER OTHER RATE RESPONSIVE INDICATOR

REFERENCE TO PRIOR RELATED PATENTS

This application is a divisional of U.S. application Ser. No. 08/343,166, filed Nov. 22, 1994 issued Jun. 4, 1996 as U.S. Pat. No. 5,522,859, which itself is a continuation-in-part of U.S. application Ser. No. 08/129,631, filed Sep. 29, 1993 and now abandoned.

BACKGROUND OF THE INVENTION

1. Field of the Invention

The present invention relates to dual chamber, rate-responsive pacemakers.

2. Description of the Prior Art

Dual chamber pacing modes have been widely adopted for pacing therapy. Among the dual chamber operating modes is the "DDD" mode, which can pace an atrium and a ventricle, senses both the atrium and the ventricle, and can either inhibit or trigger pacing stimuli for both chambers. This mode has a sensor augmented variant mode called "DDDR", where the "R" stands for rate-adaptive or rate modulation.

A DDD pacemaker includes an atrial sense amplifier to detect atrial depolarizations of the heart, and a ventricular sense amplifier to detect ventricular depolarizations of the heart. If the atrium of the heart fails to beat within a predefined time interval (atrial escape interval), the pacemaker supplies an atrial stimulus to the atrium through an appropriate lead system. Following an atrial event (either sensed or paced) and an atrioventricular (A-V) interval, the pacemaker supplies a ventricular pacing stimulus to the ventricle through an appropriate lead system, if the ventricle fails to depolarize on its own. Pacemakers which perform this function have the capability of tracking the patient's natural sinus rhythm and preserving the hemodynamic contribution of the atrial contraction over a wide range of heart rates.

Many patients have an intact sinoatrial (SA) node, but inadequate AV conduction. For these patients, the DDD mode, which attempts to pace the ventricles in synchrony with the atria, is generally adequate for their needs. Patients with Sick Sinus Syndrome (SSS) have an atrial rate which can either be sometimes appropriate, sometimes too fast, and sometimes too slow. For SSS patients, the DDDR mode provides some relief by pacing the atria and ventricles at a sensor rate determined by a sensor which senses a physiological indicator of the patients' metabolic needs. However, sensor rates are sometimes too high and sometimes too low for a variety of reasons, including, errors related to the input of programmable parameters, limitations of the sensor's ability to accurately sense the physical quantity being sensed, and limitations or problems with the algorithm used to determine the sensor rate.

In addition to the above problems, pacemakers operating in prior art sensor driven pacing modes pace at the sensor rate (and overdrive the atrium) whenever the sensor rate exceeds the sinus rate, even when the sinus rate is actually appropriate, and even when the difference between the two rates is too small to provide any discernible benefit in pacing at the higher sensor rate. Inappropriate sensor rate pacing can lead to unnecessary overdrive of the atrium, and unwarranted expenditure of battery energy.

In commonly assigned U.S. Pat. No. 5,144,949, incorporated herein by reference in its entirety, a DDDR pacemaker is disclosed wherein the operating or pacing mode is switched between the DDD, DDIR and VVIR modes as a function of the difference between the Average Atrial Rate (AAR) and the Average Combined Sensor Rate (ACSR). The DDD pacing mode (which is not a sensor driven pacing mode) is preferred as long as the AAR and ACSR are within a user selected range, and the AAR does not exceed the Atrial Upper Rate Limit (AURL) or is not irregular at higher rates. When significant atrial tachyarrythmias are detected, the VVIR mode is preferred to avoid inappropriate atrial tracking, atrial competitive pacing and risk of inducing more atrial arrhythmias. During episodes of sinus bradycardia and chronotropic atrial incompetence, the atrial rate is not adequate, so the DDIR mode is preferred. The rise up and fall back pacing rates are smoothed by taking place over several heart beats or a predetermined time interval during mode switch transitions.

The mode switching depends on the comparison of the AAR and ACSR up to the AURL and the Sensor Upper Rate Limit (SURL). Generally, when the AAR is within a first range exceeding the ACSR and both are below the AURL and the SURL, DDD pacing is maintained. When the AAR rises out of that range, then the mode is switched to VVIR. Similarly, when the ACSR is within a second range exceeding the AAR, DDD pacing is also maintained. When the second range is exceeded by the ACSR, the mode is switched to DDIR.

When in the DDIR mode, the pacing rate is limited by the SURL, and the mode is switched to DDD when the Instantaneous Atrial Rate (IAR) equals the ACSR. In the DDD mode, the pacing rate is limited to the AURL, and the mode is switched to VVIR when the ACSR falls below the SURL while the AAR remains above the AURL.

In the '949 patent, the first and second ranges are derived as functions f(A-S) and f(S-A) of the AAR and ACSR between the minimum rate and the AURL and SURL and are programmable by the physician. Thus, the actual instantaneous ranges vary as a function of the current AAR and ACSR values.

The '949 patent emphasizes the desirability of maintaining DDD pacing at an atrial escape or A-A escape interval derived from the AAR whenever possible. That is, the DDD mode is forced and departed from only under the conditions described above. The instantaneous pacing escape interval/rate are determined by the measured intervals between atrial events used to formulate the AAR while in the DDD operating mode. The ACSR is also derived independently and only resorted to to set the pacing escape interval/rate in the modes where atrial synchrony is departed from under the above described conditions.

In further U.S. Pat. No. 4,856,523, a rate-responsive pacemaker with automatic mode switching and/or variable hysteresis rate is described. A physiological, activity related, sensor develops a physiologic escape interval/rate between a minimum and a maximum rate limit (SURL) as shown in FIG. 3A thereof. A variable hysteresis escape interval setting a hysteresis rate below the physiologic rate is defined as shown in FIGS. 3B and 4 thereof. In a single chamber, rate-responsive mode, e.g. VVIR mode, if the prevailing V-V escape interval times out and a V-PACE pulse is delivered, then the physiologic escape interval is employed as the next V-V escape interval. If a V-SENSE event occurs in the prevailing escape interval, then the variable hysteresis escape interval is used as the next escape V-V interval. Use of the variable escape interval continues up to the maximum rate which is the SURL less the maximum hysteresis rate increment as shown in FIG. 3B.

The '523 patent emphasizes the importance of switching the pacing mode from the prevailing dual chamber pacing mode to a single chamber mode (typically VVIR) at high pacing rates because the contribution of the atria to cardiac output diminishes at high heart contraction rates while the energy consumption demanded by dual chamber pacing increases. In the dual chamber DVIR mode described and depicted in FIG. 6 thereof, the V-A interval is selected to be either the physiologic escape interval, or the hysteresis interval depending on whether or not a V-SENSE event is detected in the A-V interval. At high rates, the mode is preferably switched to the VVIR mode.

In a further U.S. Pat. No. 5,074,304, a dual chamber, rate-responsive pacemaker is described which correlates the atrial upper rate limit, designated HSR in this patent, to the sensor rate designated KA to allow upper rate tracking to vary with the physiologic sensor rate.

Despite these advances in dual chamber, rate responsive pacemakers, a need exists for a simple system that reliably allows the synchronized pacing rate to preferentially track the underlying sinus rate even if the sensor-derived pacing rate indicates a higher rate, where the underlying sinus rate is near to the sensor-derived pacing rate, so that the DDDR pacing mode is maintained.

SUMMARY OF THE INVENTION

In view of the above, it is an object of the present invention to provide a novel dual chamber pacemaker with rate modulation capabilities, which does not overdrive the atrium with a higher sensor rate, when the sinus rate is appropriate for the current physiologic demand on the patient's heart.

It is a further object of the present invention to operate a dual chamber, rate responsive pacemaker preferentially in the DDDR mode at a physiologic sensor derived V-A escape interval while allowing an atrial sinus tracking function to be followed on a beat-to-beat basis in patient's having reasonable chronotropic competence when the underlying sinus rate is appropriate to the sensor derived rate.

There is provided in accordance with the present invention, a rate-responsive pacemaker for pacing a patient's heart at a pacing rate, at least including the means for and steps of:

generating pacing pulses and applying the pulses to a chamber of a patient's heart;

sensing depolarizations of the heart chamber;

determining the physiologic demand on the patient's heart;

defining physiologic escape intervals as a function of the physiologic demand on the patient's heart which establish a physiologic pacing rate;

in response to sensing of a depolarization of the heart chamber, adding incremental intervals to a predetermined number of the physiologic escape intervals to define prolonged sinus escape intervals which allow for sensing underlying heart depolarizations recurring at a slower sinus rate than the physiologic pacing rate;

triggering generation of a pacing pulse on expiration of the prolonged escape interval; and in response to a failure to sense depolarizations of the heart chamber within the prolonged sinus escape intervals, gradually decrementing the duration of the incremental intervals over a series of the prolonged sinus escape intervals.

In a preferred embodiment, the rate responsive pacemaker is preferably a dual chamber, rate-responsive pacemaker pulse generator adapted to be attached with atrial and ventricular pacing and sensing electrodes and comprising atrial and ventricular sense amplifiers for sensing natural atrial and ventricular depolarizations as atrial and ventricular sensed events, respectively, and atrial and ventricular pulse generators for providing atrial and ventricular pacing pulses to the patient's atrium and ventricle, respectively, at an adjustable pacing rate dependent on the patient's natural atrial depolarization rate and upon the patient's physiologic needs for cardiac output, wherein the pacemaker operates in accordance with the steps of and means for:

sensing the level of patient activity and providing a patient activity sensor signal related to the patient's physiologic need for cardiac output;

providing a sensor-derived ventricle-to-atrium (V-A) escape interval responsive to the patient activity sensor signal and related to patient activity;

establishing an atrial-to-ventricular (A-V) time delay interval and timing the delivery of a ventricular pacing pulse by the ventricular pulse generator after a preceding atrial sensed event or atrial pacing pulse, whereby the time out of an V-A escape interval followed by the time out of an A-V time delay interval constitutes a pacing cycle and defines a physiologic atrial and ventricular pacing rate in relation to patient activity;

timing out the sensor-derived V-A escape interval upon detection of a ventricular sensed event during the A-V time delay or upon delivery of a ventricular pacing pulse;

operating the atrial sense amplifier to sense the occurrence of an atrial depolarization during at least a portion of the sensor derived V-A escape interval as an atrial sensed event;

operating the atrial pulse generator to deliver an atrial pacing pulse at the end of the V-A escape interval in the absence of an atrial sensed event;

providing a sinus preference time window in response to an atrial sensed event in the sensor-derived V-A escape interval;

providing a prolonged V-A escape interval of the following pacing cycles prolonged by the sinus preference time window to provide synchronized ventricular pacing in response to atrial sinus depolarizations, if present, in the prolonged V-A escape interval; and gradually decrementing the durations of the sinus preference time windows over a series of the prolonged escape intervals in response to a failure to sense an atrial sinus depolarization within the series of prolonged V-A escape intervals in order to gradually restore the sensor-derived V-A escape interval.

In its various embodiments, the apparatus and methods of the present invention further comprise the means for and steps of periodically searching for an underlying sinus rhythm of the heart chamber by periodically adding the incremental interval (sinus preference window) to the sensor-derived escape interval to determine if a depolarization will be sensed, and, if present, retaining the prolonged escape interval as long as the sinus depolarizations are sensed.

In a further aspect of the invention, the apparatus and methods further comprise the means for and steps of measuring the elapsed time during the prolonged escape intervals until the sensing of a depolarization occurs, and, if the sensed depolarization is measured within the sensor-derived escape interval, adding the incremental interval to the measured escape interval rather than the sensor-derived escape interval in setting the succeeding prolonged escape interval.

In a still further aspect of the invention, the apparatus and methods comprise the means for and steps of adding the full incremental interval to the measured escape interval or the sensor-derived escape interval in setting the succeeding prolonged escape interval in all cases where the depolarization is sensed in a preceding prolonged escape interval with a decremented duration, incremental interval.

The details of the present invention will be revealed in the following description, with reference to the attached drawing.

BRIEF DESCRIPTION OF THE DRAWING

In the various figures of the drawing, like reference numerals indicate identical structures throughout the several views, and the elements are numbered such that the left-most digit corresponds to the drawing figure in which an element first appears.

DETAILED DESCRIPTION OF THE PREFERRED EMBODIMENTS

Figure 1:
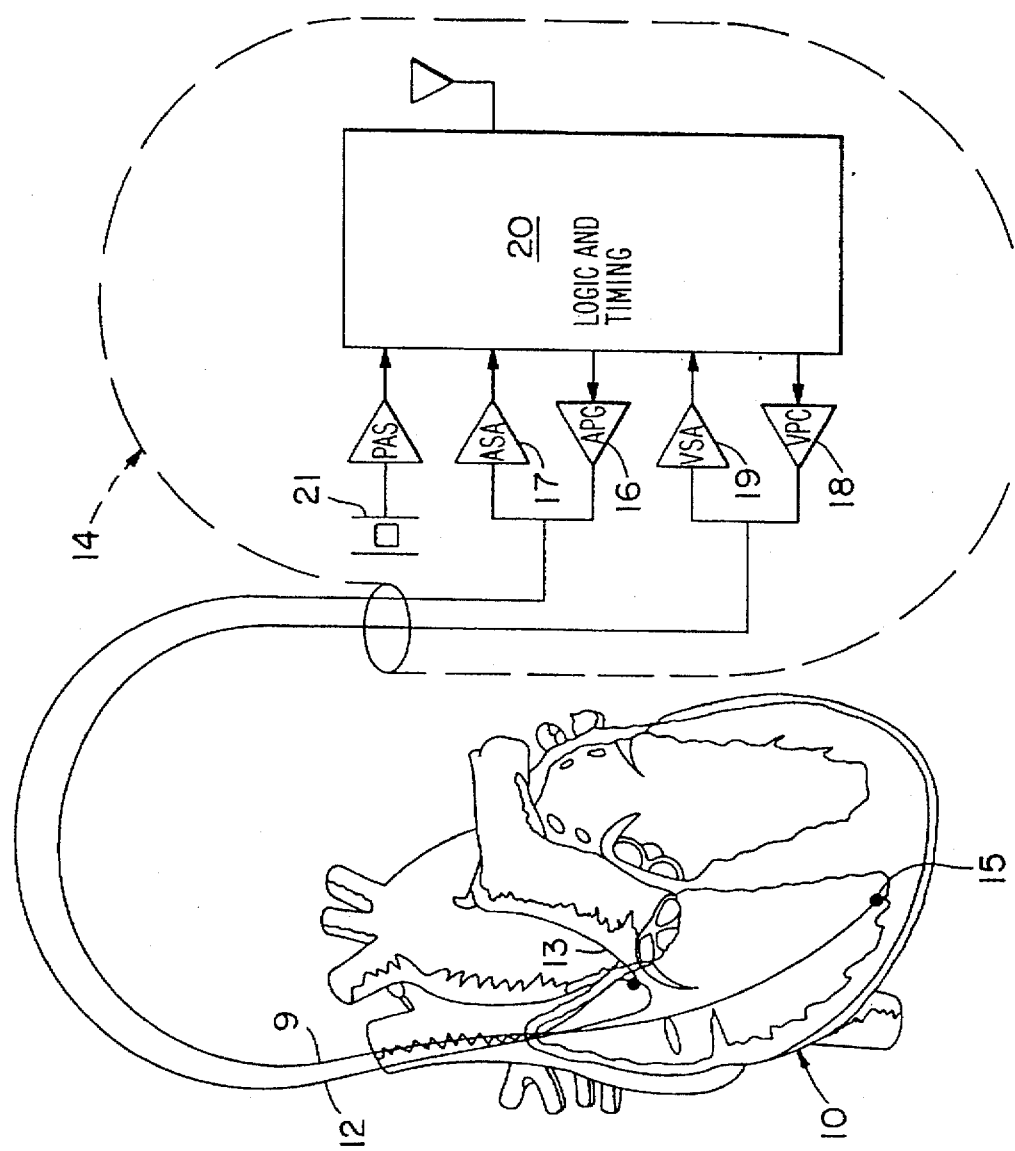
FIG. 1 is block level diagram of a DDDR pacemaker capable of implementing the Sinus Preference Algorithm of the present invention.

The present invention may be incorporated into such prior art pacemakers as, for example, DDD pacemaker taught by U.S. Pat. No. 4,312,355 to Funke, hereby incorporated by reference. Another rate-responsive pacemaker suitable for use with the invention is taught in U.S. Pat. No. 4,951,667 to Markowitz et.al., hereby incorporated by reference, which teaches a dual chamber, activity-based, rate-responsive pacemaker of the DDDR type. This pacemaker utilizes sensed patient activity to set the pacemaker's "sensor" rate. The present invention is preferably implemented in multiprogrammable pacemaker of a type known in the prior art FIG. 1 is block level diagram which sets forth the structures required to incorporate the invention into a DDD/DDDR pacemaker. In the drawing, the patient's heart 10 has an atrial pacing lead 12 passed into the right atrium and a ventricular lead 9 passed into the right ventricle. The atrial lead 12 has an atrial electrode array 13 which couples the pacemaker 14 to the atrium. The ventricular lead 9 has a ventricular electrode array 15 for coupling the pacemaker 14 to the ventricular tissue of a patient's heart 10.

The atrial electrode array 13 is coupled to both an atrial pace stimulus generator 16 (APG), and an atrial sense amplifier 17 (ASA). In a similar fashion, the ventricular electrode array 15 is coupled to a ventricular pace stimulus generator 18 (VPG) and a ventricular sense amplifier 19 (VSA). Although the arrangement in FIG. 1 uses a unipolar configuration, it can be easily modified to use a bipolar configuration, as well.

FIG. 1 shows a preferred patient activity sensor (PAS) 21 and appropriate signal conditioning circuitry, which can be provided to alter the pacemaker operation in response to the sensed motion of the patient. An appropriate activity-based, rate-responsive system is taught by U.S. Pat. No. 4,428,378 to Anderson et al., which is incorporated by reference herein. It should be appreciated that alternate sensors of a physiologic parameter indicative of physiologic demand on a patient's heart can be provided to achieve rate and post-ventricular atrial refractory period (PVARP) variation based upon other sensed physical parameters.

In general, the atrial sense amplifier ASA 17 detects depolarizations of atrial tissue and generates an atrial sensed event (ASE) to indicate the detection of an atrial beat of the patient's heart. Similarly, the ventricular sense amplifier VSA 19 responds to a ventricular beat of the patient's heart and generates a corresponding ventricular sensed event (VSE).

The pacemaker logic 20, which is coupled to the sense amplifiers, generates various time intervals in response to detected atrial and ventricular sensed events, and generates both atrial paced event (APE) and ventricular paced event (VPE) signals in response to timer logic and the sense amplifier signals. The principal timing functions are set forth in Table 1, below.

TABLE 1

| Timer | Timing Functions | |
|---|---|---|
| | Starting Events(s) | Ending Event(s) |
| PPVARP & VRP | VPE or VSE | Timeout |
| ARP | APE or VPE | Timeout |
| V-A (DDDR) or V-A (DDD) | VSE or VPE | APE |
| URL | VSE or VPE | Timeout |
| A-VD | APE or ASE | VPE or VSE |
| RLI | VSE or VPE | Timeout |
| Disable Interval (T) | VPE | Timeout |

For example, timer logic 20 is provided with means to time out a programmed A-V delay period (AVD). The A-V delay period is initiated by the occurrence of either an atrial sensed or atrial paced event. The A-V delay period may end with the generation of a ventricular paced event (VPE) or on sensing a ventricular sensed event (VSE).

Logic and timing circuit 20 also provides for a programmed post-ventricular atrial refractory period (PPVARP). The PPVARP period begins with either a ventricular paced event (VPE) or a ventricular sensed event (VSE), and expires at the conclusion of a physician-set time interval. Logic and timing circuit 20 similarly defines a ventricular refractory period (VRP) following either a VSE or VPE, which is typically shorter than the portion of the PPVARP following a VSE or VPE. In the case of an ectopic VSE, both a VRP and a PPVARP may be generated. Logic and timing circuit 20 also defines an atrial refractory period (ARP) following either a ASE or APE.

The logic 20 also times out a refractory limit interval (RLI) which begins with the occurrence of a ventricular sensed or paced event. Pacemaker logic 20 also times out a disable interval period T of a fixed but physician-selected duration. This disable interval time period begins upon the occurrence of a VPE in a pacing cycle where the next post-ventricular atrial refractory period is extended. Typically, digital pacemaker logic and timing circuit 20 defines an atrial blanking interval following delivery of an APE pulse, during which atrial sensing is disabled, as well as ventricular blanking intervals following atrial and ventricular pacing pulse delivery, during which ventricular sensing is disabled.

Pacemaker logic 20 also times out an upper rate limit interval (URL). This timer is initiated by the occurrence of a VPE or VSE, and limits the upper rate at which ventricular stimuli are delivered to the heart.

Preferably two separate lower rate V-A interval timer functions are provided. The first is set by the physician when the base pacing rate is selected. This DDD V-A time interval starts from the occurrence of a VPE or VPE, and provided neither an ASE nor a VSE occurs during the V-A time interval, an APE is generated after the expiration of the V-A time interval. The duration of the second lower rate time interval is a function of the measured patient activity acquired by the activity sensor 21. Typically, this DDDR V-A time interval begins with a sensed or paced ventricular event (VSE or VPE, respectively) and has a time duration reflecting patient activity. In this art, such structures are well known, and a variety of techniques can be used to implement the required timer functions.

The pacemaker logic 20 is also coupled to paced event pulse generators 16 and 18. For example, atrial paced event signals are coupled to the atrial pace stimulus generator 16 to produce an atrial pacing stimulus while the ventricular paced event signal generates a ventricular pacing stimulus through the ventricular pace stimulus pulse generator 18. Pacemaker logic 20 thus defines the basic pacing or escape interval over a pacing cycle, which corresponds to a successive A-V interval and V-A interval.

Figure 7:
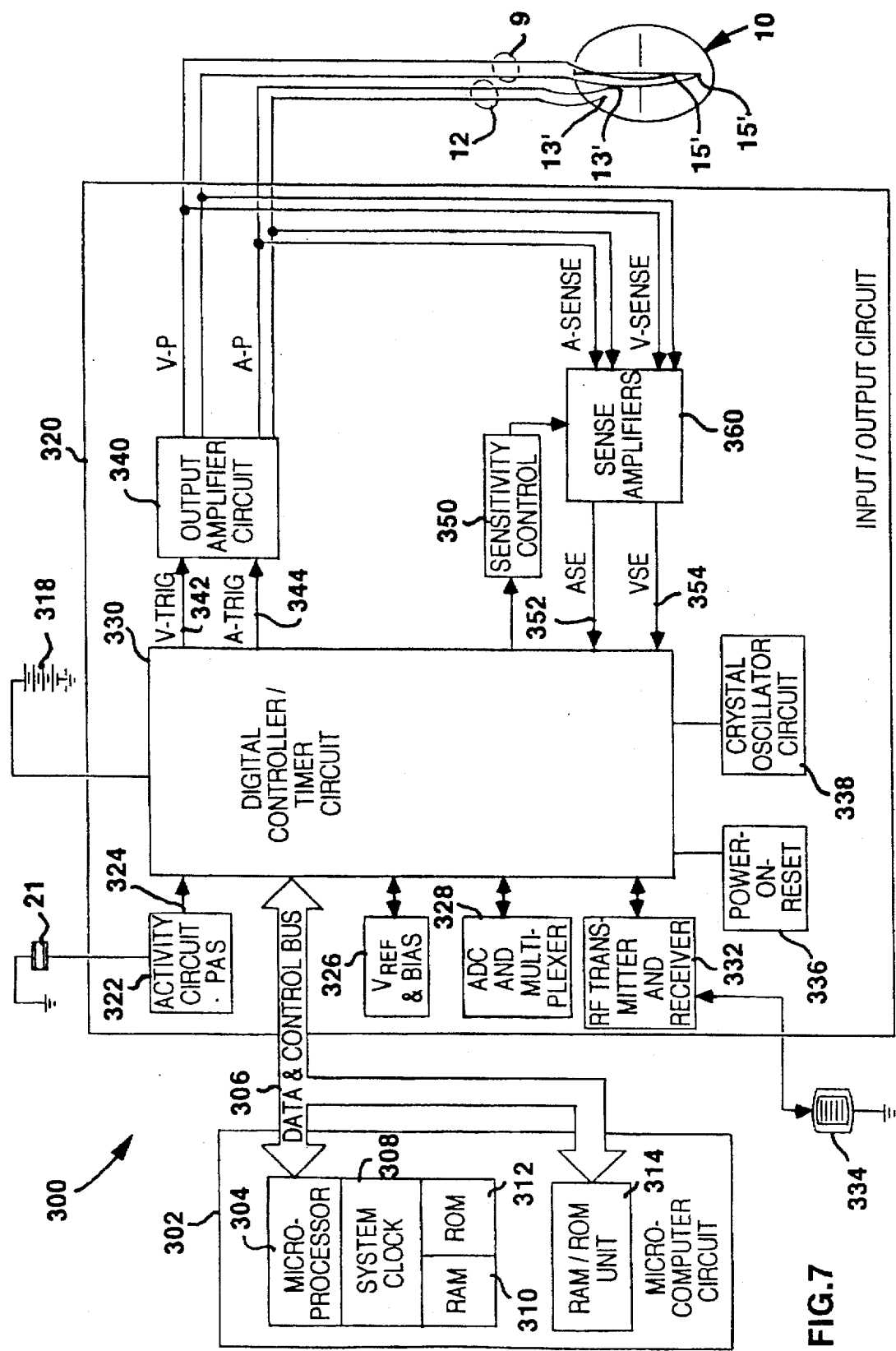
FIG. 7 is a block diagram of the dual chamber pacemaker illustrated in FIG. 1, illustrating the logic and timing components in more detail.
Figure 8:
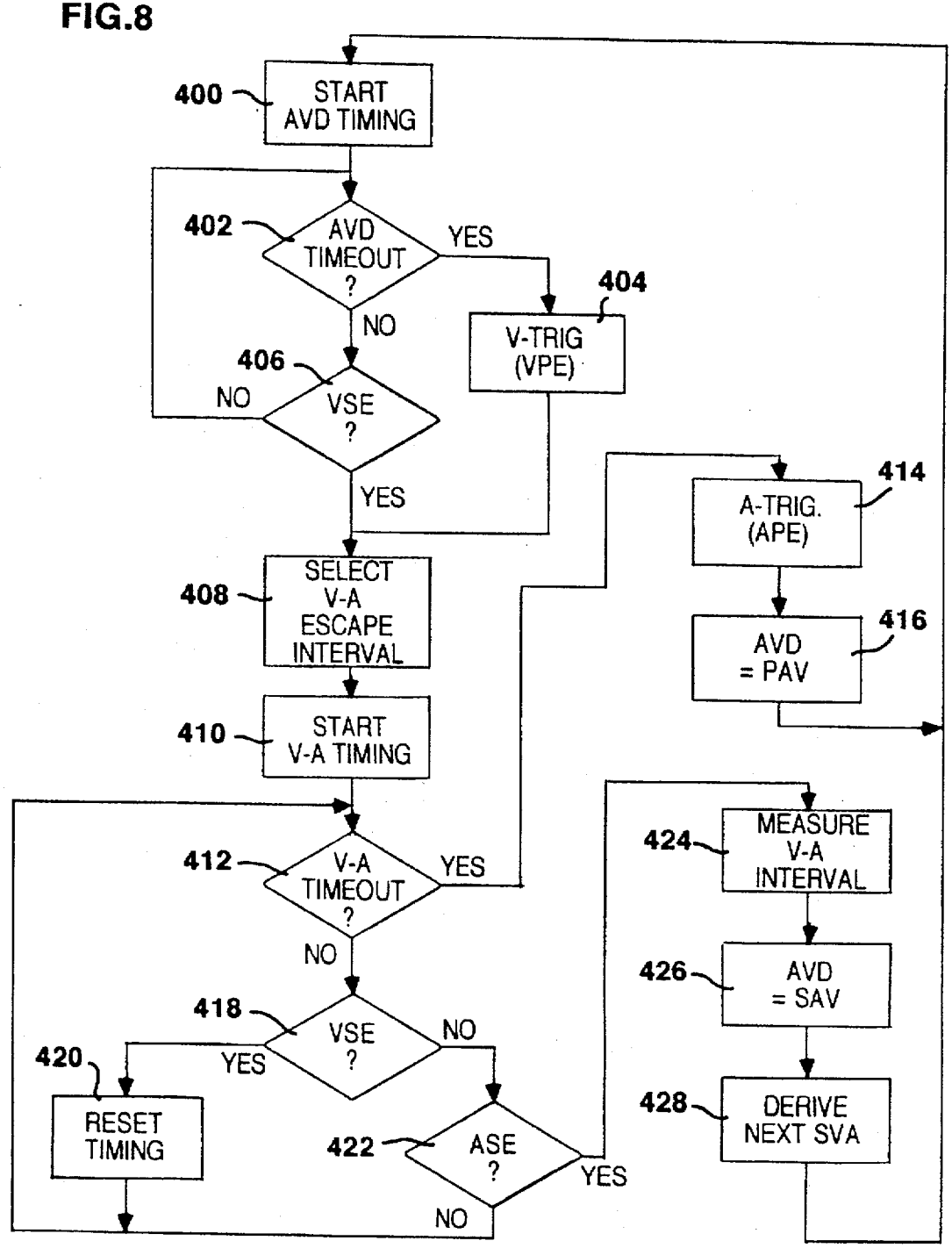
FIG. 8 is a flowchart of the overall operation of the pacemaker of FIG. 7.

Turning now to FIGS. 7 and 8, they depict the pacemaker of FIG. 1 and summarize its conventional operation in greater detail. The IPG circuit 300 of FIG. 7 is divided generally into a microcomputer circuit 302 and a pacing circuit 320. The pacing circuit 320 includes the ASA 17 and VSA 19 of FIG. 1 as the output amplifier circuit 340 and the APG 16 and the VPG 18 in the sense amplifiers 360. The output circuit 340 and sense amplifier circuit 360 may contain pulse generators and sense amplifiers corresponding to any of those presently employed in commercially marketed cardiac pacemakers. The bipolar leads 9 and 12 are illustrated schematically as coupled directly to the input/output circuit 320. However, in the actual implantable device they would, of course, be coupled by means of removable electrical connectors inserted in the connector block illustrated in broken lines 14 in FIG. 1.

Sensed atrial depolarizations or P-waves that are confirmed by the atrial sense amplifier (ASE) in response to an A-sense are communicated to the digital controller/timer circuit 330 on ASE line 352. Similarly, ventricular depolarizations or R-waves that are confirmed by the ventricular sense amplifier in response to a V-sense are communicated to the digital controller/timer circuit 330 on VSE line 354.

In order to trigger generation of a ventricular pacing or VPE pulse, digital controller/timer circuit 330 generates a trigger signal on V-trig line 342. Similarly, in order to trigger an atrial pacing or APE pulse, digital controller/timer circuit 330 generates a trigger pulse on A-trig line 344.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexor circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexor 328, power-on-reset circuit 336 and crystal oscillator circuit 338 may correspond to any of those presently used in current marketed implantable cardiac pacemakers.

Figure 2:
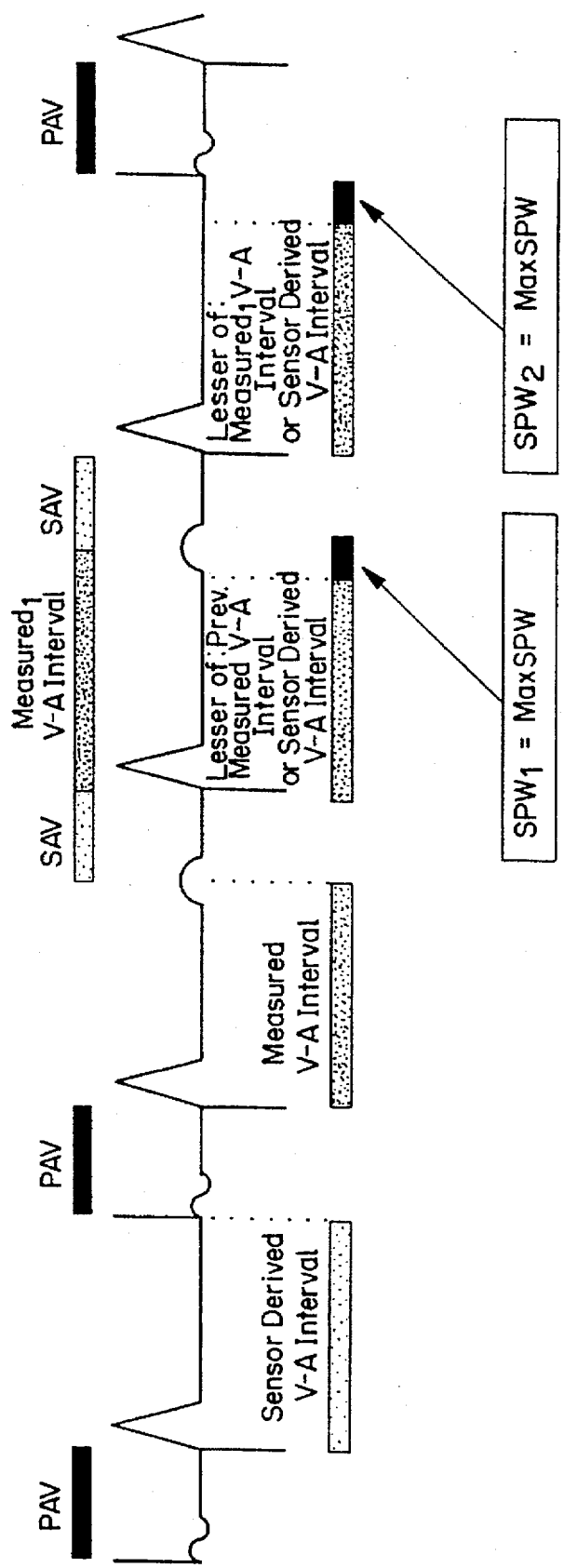
FIG. 2 is a timing diagram depicting Sinus Preference Windows of the present invention in response to atrial paced and sensed events.

Data transmission to and from the external programmer 40 illustrated in FIG. 2 is accomplished by means of the telemetry antenna 334 and an associated RF transmitter and receiver 322, which serves both to demodulate received downlink telemetry and to transmit uplink telemetry. For example, circuitry for demodulating and decoding downlink telemetry may correspond to that disclosed in U.S. Pat. No. 4,556,063 issued to Thompson et al. and U.S. Pat. No. 4,257,423 issued to McDonald et al., while uplink telemetry functions may be provided according to U.S. Pat. No. 5,127,404 issued to Wyborny et al. and U.S. Pat. No. 4,374,382 issued to Markowitz. Uplink telemetry capabilities will typically include the ability to transmit stored digital information as well as real time or stored EGMs of atrial and/or ventricular electrical activity (according to the teaching of the above-cited Wyborny patent), as well as transmission of Marker Channel pulses indicating the occurrence of sensed and paced depolarizations in the atrium and ventricle, as disclosed in the cited '382 Markowitz patent.

Control of timing and other functions within the pacing circuit 320 is provided by digital controller/timer circuit 330 included in logic and timing block 20 of FIG. 1, which includes a set of timers and associated logic circuits connected with the microcomputer 302. Microcomputer 302 controls the operational functions of digital controller/timer 324, specifying which timing intervals are employed, and controlling the duration of the various timing intervals of Table 1, via data and control bus 306. Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 is interrupt driven, operating in a reduced power consumption mode normally, and awakened in response to defined interrupt events, which may include the A-trig, V-trig, ASE and VSE signals. The specific values of the intervals defined are controlled by the microcomputer circuit 302 by means of data and control bus 306 from programmed-in parameter values and operating modes.

As described above, if the IPG is programmed to a rate responsive mode, the patient's activity level is monitored periodically, and the sensor derived V-A escape interval is adjusted proportionally. A timed interrupt, e.g., every two seconds, may be provided in order to allow the microprocessor 304 to analyze the output of the activity circuit (PAS) 322 and update the basic V-A escape interval employed in the pacing cycle. The microprocessor 304 may also define variable A-V intervals and variable ARPs and VRPs which vary with the V-A escape interval established in response to patient activity.

Digital controller/timer circuit 330 thus defines the basic pacing or escape interval over a pacing cycle which corresponds to a successive A-V interval and V-A interval. As a further variation, digital controller/timer circuit 330 defines the A-V delay intervals as a SAV that commence following a sensed ASE and a PAV that commences following a delivered APE, respectively.

Digital controller/timer circuit 330 also starts and times out the intervals set forth above in Table 1 for controlling operation of the ASA and VSA in sense amplifier circuit 360 and the APG and VPG in output amplifier circuit 340. Typically, digital controller/timer circuit 330 defines an atrial blanking interval following delivery of an APE pulse, during which atrial sensing is disabled, as well as ventricular blanking intervals following atrial and ventricular pacing pulse delivery, during which ventricular sensing is disabled. Digital controller/timer circuit 330 also defines the ARP during which atrial sensing is disabled or the ASE is ignored for the purpose of resetting the V-A escape interval. The ARP extends from the beginning of the SAV or PAV interval following either an ASE or an A-trig and until a predetermined time following sensing of a ventricular depolarization or triggering the delivery of a VPE pulse. The durations of the ARP, PVARP and VRP may also be selected as a programmable parameter stored in the microcomputer 302. Digital controller/timer circuit 330 also controls sensitivity settings of the sense amplifiers 360 by means of sensitivity control 350.

The illustrated IPG block diagram of FIG. 7 is merely exemplary, and corresponds to the general functional organization of most multi-programmable microprocessor controlled DDD(R) cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 312 of the microcomputer circuit 302. However, the present invention may also be usefully practiced by means of a full custom integrated circuit, for example, a circuit taking the form of a state machine, in which a state counter serves to control an arithmetic logic unit to perform calculations according to a prescribed sequence of counter controlled steps. As such, the present invention should not be understood to be limited to a pacemaker having an architecture as illustrated in FIG. 1 or 7, and a circuit architecture as illustrated in FIG. 1 or 7 is not believed to be a prerequisite to enjoying the benefits of the present invention.

FIG. 8 is a functional flow chart of the overall pacing cycle timing operation of the pacemaker illustrated in FIGS. 1 and 7 in DDDR pacing mode. For the sake of simplicity, functional steps corresponding to the provision of the ARP, VRP, PPVARP, blanking periods and delivery of VPE and VSE have been omitted, to allow for easier understanding of the overall timing operations. In the flow chart of FIG. 8, it is assumed that the basic pacing cycle timing of the pacemaker is based on the definition of a sensor-derived V-A escape interval (SVA) and may reflect the Sinus Preference Window (SPW) in a manner further set forth in the flowchart of FIGS. 9 and 10 described below.

At block 400, the V-A interval is first reset in response to an ASE or APE, and timing of the current A-V delay interval (AVD) is commenced. During the A-V delay interval, the system awaits either time out of the current A-V delay interval (PAV or SAV) at block 402 or ventricular sensing at block 406. If a VSE does not occur at block 406 prior to A-V delay interval time out, a VPE is generated at block 404 at the end of the A-V interval. When the VSE or the VPE occurs, the pacemaker's timing may be reset at block 408 to select a V-A escape interval, which is either be the sensor-derived V-A escape interval or the prolonged V-A escape interval defined in the manner shown in the flowchart of FIGS. 9 and 10 described below. Then the selected V-A delay interval is timed out at block 410.

The algorithm awaits expiration of the V-A escape interval at block 412. If the V-A escape interval expires at block 412 without any intervening ASE or VSE sensing, an APE pulse is generated at block 414. The next succeeding A-V delay interval is defined to be equal to PAV at block 416, and the A-V timing is commenced again at block 400.

Sensing of a VSE at block 418 outside of the VRP causes the V-A interval timing to be reset in block 420 and the reset V-A interval to be restarted in block 412. A VSE sensed at this point is not effective to trigger an update of the SAV and PAV intervals. If an ASE is sensed in the V-A interval at block 422, then the V-A interval is measured and stored in block 424. In this regard, if the current sensor-derived V-A escape interval is a prolonged V-A escape interval selected in any of the ways to include all or part of a SPW, the measured V-A interval may be longer than the sensor-derived V-A escape interval. As described hereafter, the next V-A escape interval may be derived from the measured V-A interval in block 428 and used in block 408 during the next pacing cycle. The next A-V delay interval is set to SAV in block 426, and the A-V interval is restarted in block 400.

The time interval values for the parameters of Table 1 employed in the algorithm of FIG. 8 and any other time intervals defined by operating algorithms at any particular time are stored in either ROM or RAM and are fetched and used as described above. Thus, in the operations of the IPG in either the general timing algorithm of FIG. 8 or in the SPW algorithm of the present invention described below, the specified time intervals may be fetched and employed in each designated step in response to the trigger or event signals designated in any of the algorithms.

SUMMARY OF THE SINUS PREFERENCE ALGORITHM OPERATION

As with prior art pacemakers, a pacemaker employing the Sinus Preference Algorithm of the present invention, a unique variant of the DDDR mode, tracks the sinus rate when the sinus rate exceeds the sensor rate. Unlike prior art pacing algorithms for operating in the DDDR mode, the Sinus Preference Algorithm does not always cause the pacemaker to pace at the end of the sensor derived escape interval whenever the sensor rate exceeds the sinus rate. The pacemaker 14 paces at the sensor rate, or a variation thereof, whenever the sensor rate exceeds the sinus rate by more than a programmable maximum rate drop. Otherwise, the pacemaker 14 tracks the sinus rate. The Sinus Preference Algorithm will be explained in greater detail infra., with reference to FIGS. 2–6 and in reference to the combined flowchart of FIGS. 9 and 10.

DETAILS OF THE SINUS PREFERENCE ALGORITHM OPERATION

Figure 3:
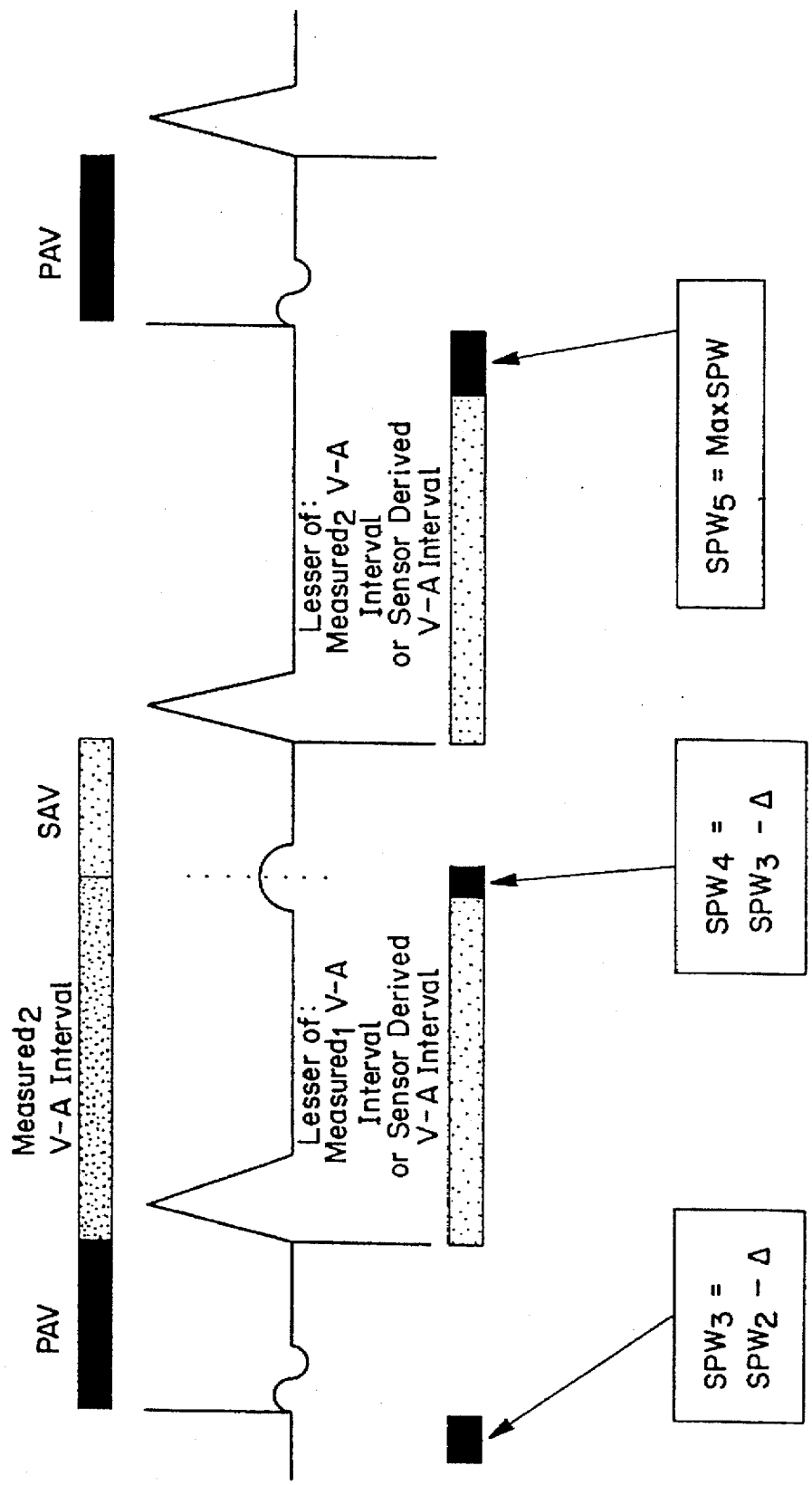
FIG. 3 is a continuation of the timing diagram in FIG. 2.

FIGS. 2 and 3 together, represent a timing diagram of an example of successive heart cycles which illustrate certain of the operations of the Sinus Preference Algorithm of the present invention in the context of the pacemaker of FIGS. 1, 7 and 8. At the beginning of the timing diagram of FIG. 2 at point 252, a ventricular paced event (VPE) occurs after an atrial paced event (APE) (point 250) and a paced atrioventricular (PAV) interval. After a sensor-derived, physiologic ventricle-to-atrium (SVA) interval (also the atrial escape interval at this time), the atrial pulse generator 16 of the pacemaker 14 (output amplifier circuit 340 of FIG. 7) again delivers a pacing stimulus APE to the atrium at point 254, thereby completing a pacing cycle commencing from the point 250. Each time that the prevailing V-A interval is timed out, it is timed so that the time of sensing of an atrial sensed event (ASE) during the V-A escape interval may be measured to derive a measured V-A interval (MVA) as shown, for example, between points 256 and 258.

Following a PAV at point 256, the VPG 18 of pacemaker 14 delivers a pacing stimulus signal VPE to the ventricle. In the first example of FIG. 2, an ASE occurs at point 258, and a measured V-A interval (less than the sensor-derived physiologic V-A interval in this instance) is derived and is followed by a sensed atrioventricular (SAV) interval and a VPE at point 260.

The occurrence of the first ASE at point 258 causes the algorithm to redefine the next atrial escape V-A interval. First, the previous measured V-A interval is compared to the sensor-derived V-A interval. If the sensor-derived V-A interval (SVA) is the lesser of the two (which can occur as shown later if the previous V-A interval is prolonged by a SPW interval), the new V-A interval is set equal to the sensor-derived V-A interval plus the current SPW (in this instance, MaxSPW).

If the previous measured V-A interval (MVA) is the lesser of the two (as in this case), the algorithm then compares the sum of the previous measured V-A interval plus the previous SPW with the sensor-derived V-A interval. The greater of the two is chosen as the new V-A escape interval to be timed from point 260. In this case, there is no prior SPW, and so the first Sinus Preference Window SPW$_1$ is set to correspond to the programmed maximum rate drop (MaxSPW) from the sensor rate allowable.

Figure 6:
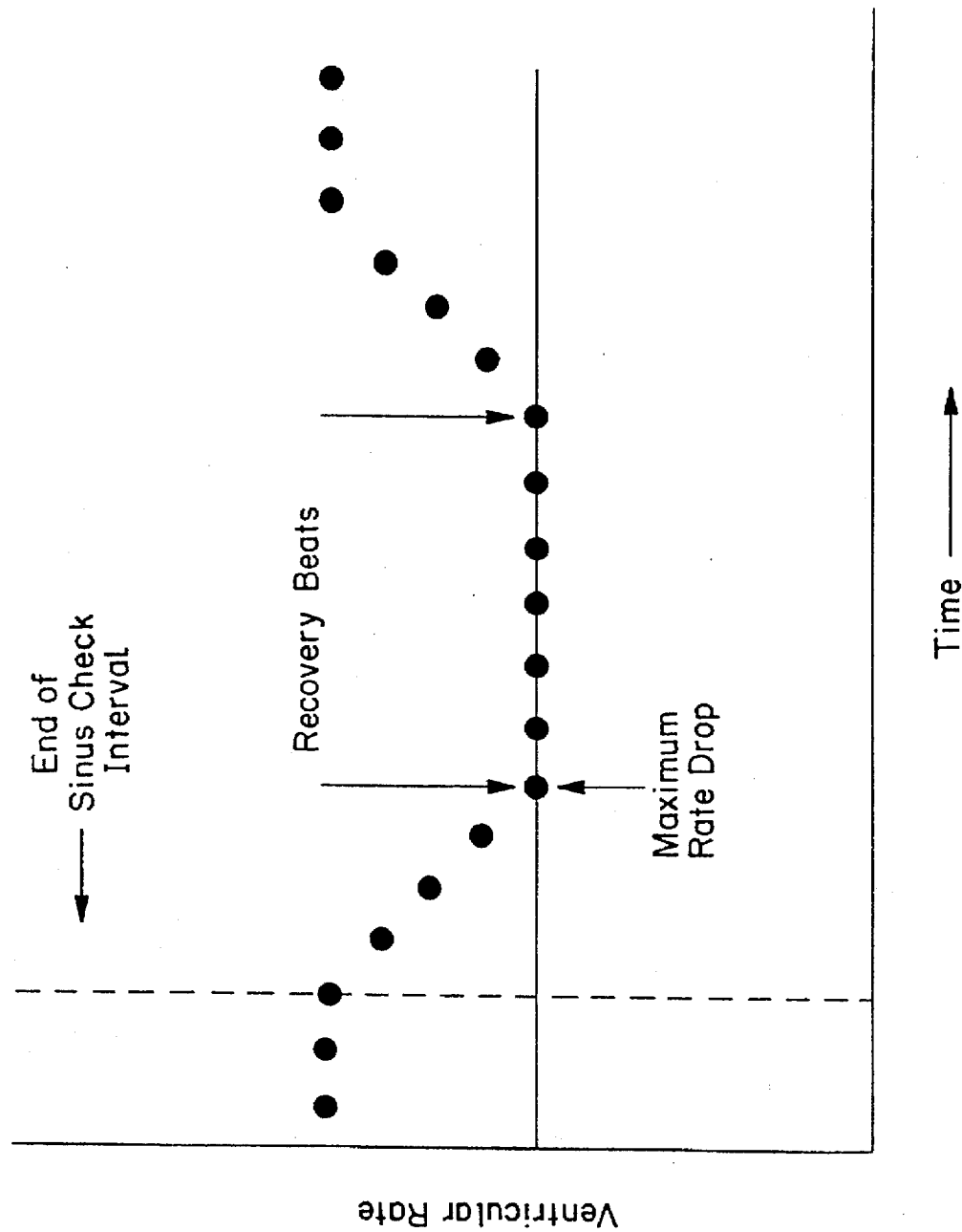
FIG. 6 is a graph of ventricular rate versus time, illustrating several recovery beats after the maximum rate drop has been reached.

The Sinus Preference Algorithm operates within the microcomputer 302 and digital controller/timer circuit 330 and endeavors to first pace at the sensor rate minus the maximum rate drop (inversely corresponding to the MaxSPW) in response to a spontaneous ASE to look for further possible ASEs, thus searching for sinus node beats occurring within acceptable proximity to the sensor rate. If found, the Sinus Preference Algorithm operates pacemaker 14 to track the sinus rate. However, if none are found or if they discontinue as shown, for example, at point 270, the pacing rate remains at the maximum rate drop level for several programmable recovery beats, e.g. the six pacing cycles at the maximum rate drop as shown in FIG. 6.

As shown in the timing diagram in FIG. 2, a second ASE occurs prior to the expiration of the prolonged V-A escape interval and within the SPW$_1$. The next Sinus Preference Window SPW$_2$ remains at MaxSPW, and the new prolonged V-A escape interval is chosen as described supra by adding the sensor-derived V-A interval with MaxSPW. Since no ASE occurs during the atrial escape interval, an APE occurs at its expiration followed in time by a VPE.

Turning to FIG. 3, it illustrates an operation of the Sinus Preference Algorithm in conjunction with the gradual rate increase from the maximum rate drop and back to the sensor-derived rate after delivery of the recovery beats. At each succeeding heart cycle following the termination of the series of recovery beats, the pacing rate (as defined by the V-A escape interval) is increased by a programmable "SPW Rate Change". From the SPW Rate Change, a corresponding delta is derived, where delta equals the inverse of SPW Rate Change, or the change in interval needed to accomplish the desired rate change. The delta is subtracted from each succeeding SPW as shown at points 274 and 278 in FIG. 3 so that the pacing rate begins to increment by the SPW Rate Change. Thus, SPW$_3$ equals SPW$_2$ minus delta, and SPW$_4$ equals SPW$_3$ minus delta.

FIG. 3 also illustrates the situation that may occur where, prior to the expiration of the atrial escape interval that includes SPW$_4$, an ASE occurs, which resets SPW$_5$ to MaxSPW. In this example, the measured V-A escape interval is longer than the sensor-derived or physiologic V-A escape interval. The lesser value is employed in setting the prolonged V-A escape interval of the next pacing cycle between points 280 and 284. If the ASE had occurred prior to the start of SPW$_4$, then the measured V-A interval would have been employed in setting the succeeding, prolonged V-A escape interval.

From point 284, and in the absence of further ASEs, the programmed number of recovery beats are delivered at the maximum rate drop as described above. The pacing rate governed by the V-A escape interval may stay at the maximum rate drop in the presence of successive ASEs, oscillate between the maximum rate drop and the intermediate pacing rates in the presence of intermittent ASEs, or return to the physiologic V-A escape interval as shown in FIG. 6.

Figure 4:
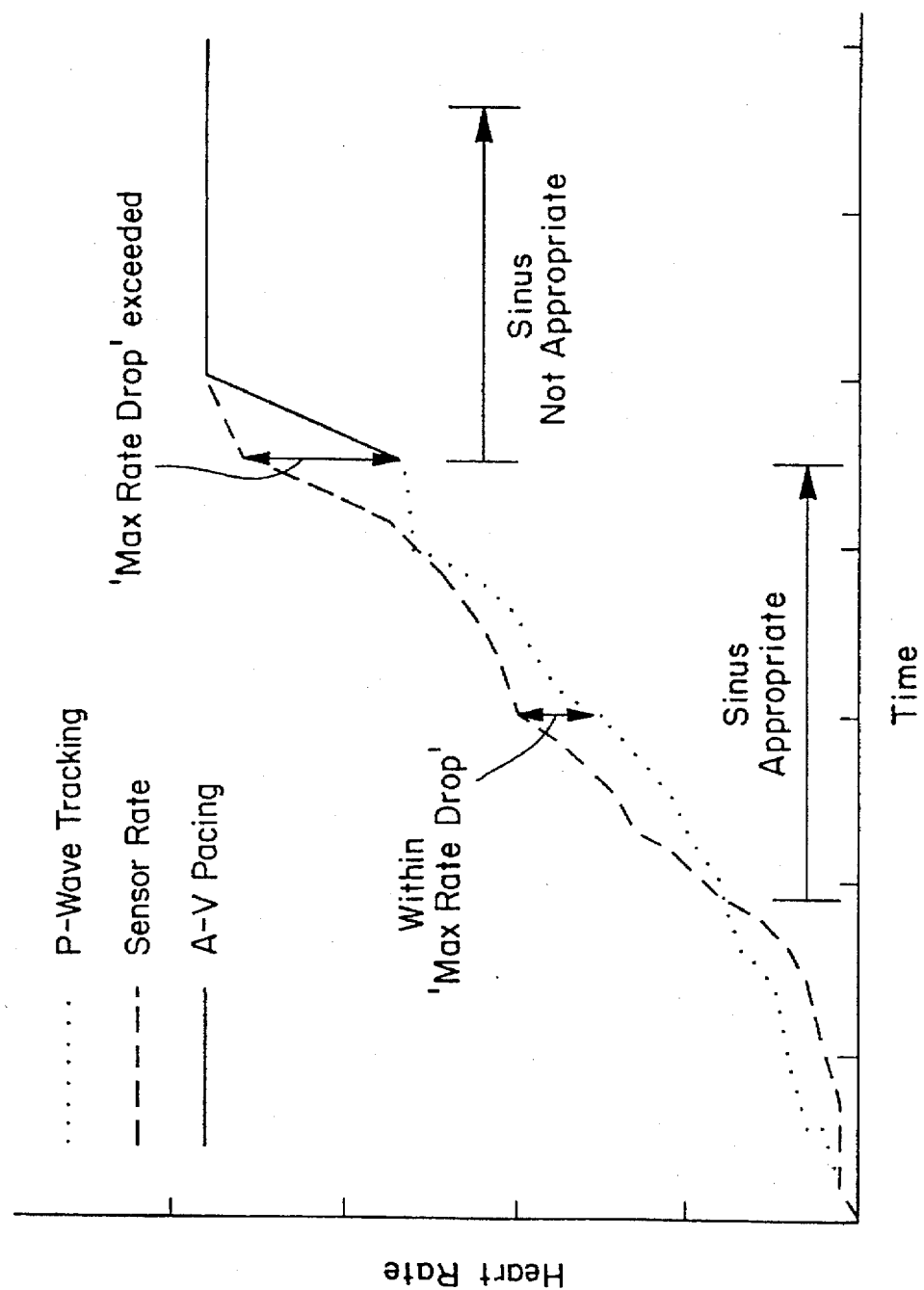
FIG. 4 is a graph of heart rate versus time using the Sinus Preference Algorithm of the present invention.

The effect of the Sinus Preference Algorithm is illustrated by the example in FIG. 4, which shows graphs of heart rate versus time for P-wave or sinus rate (dotted curve), sensor rate (dashed curve), and A-V pacing rate (solid curve). In the range of heart rates where sinus tracking is appropriate ("Sinus Appropriate"), the sensor rate does not exceed the sinus rate by more than the SPW Maximum Rate Drop (MRD). In the range of heart rates where sensor tracking is appropriate ("Sinus Not Appropriate"), the sensor rate exceeds the sinus rate by more than the SPW Maximum Rate Drop.

Figure 5:
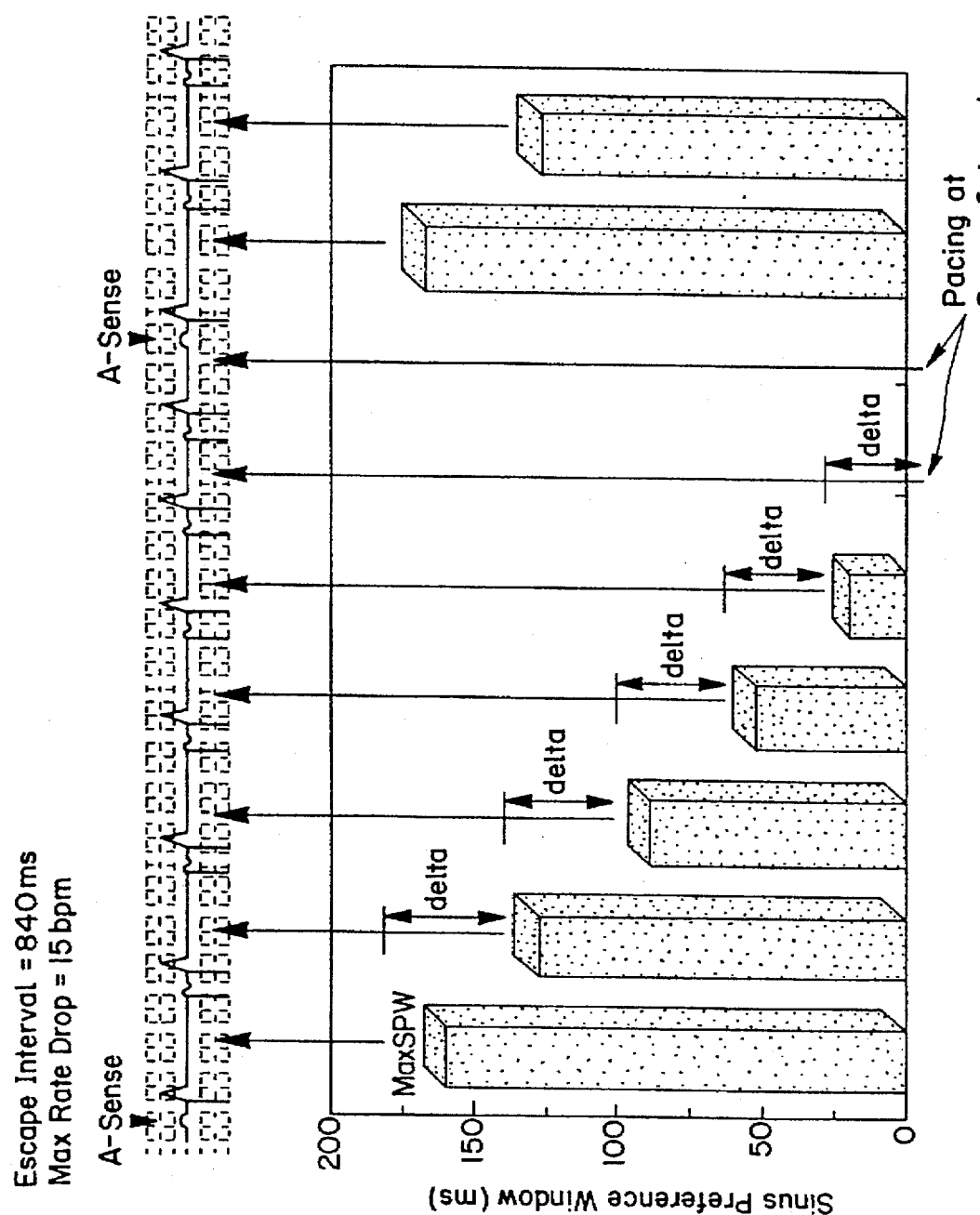
FIG. 5 is a resulting electrocardiogram in response to changing Sinus Preference Windows and the occurrence of atrial sensed events.

In the absence of ASEs or MRD exceeded in FIG. 4, the pacing rate is incremented each heart cycle by the SPW Rate Change until the sensor-derived rate is reached. To further illustrate the operation of the Sinus Preference Algorithm, FIG. 5 shows an example of an electrocardiogram (ECG) and corresponding SPWs successively shortened by delta resulting from the occurrence of either two ASEs or, in accordance with a further aspect of the invention, after a programmable Sinus Check Interval (SCI) spanning several heart cycles expires. In this "Sinus Not Appropriate" region, the rate change from the P-wave tracking rate to the sensor-derived rate is smoothed as shown in FIGS. 4 and 5. Once the SPW Maximum Rate Drop is exceeded (i.e., the pacemaker 14 reaches the end of the atrial escape interval without the occurrence of an ASE), and after the recovery beats, the pacemaker 14 begins incrementing the pacing rate until it reaches the sensor rate, where it remains until either the expiration of the SCI or the occurrence of an ASE. The occurrence of an ASE might be interpreted as the return of the sinus rate to an appropriate one for the current physiologic demand on the heart, to which the pacemaker 14 can then begin tracking again.

The SCI is a programmable time interval, or number of pacing cycles, that may be set in terms of minutes or hours by the physician in order to periodically search for an underlying sinus rhythm that would otherwise be present in the absence of pacing. The SCI is reset to zero, and begins counting each time the SPW is reset to MaxSPW. The SCI expires when its programmed maximum time or cycle count is reached. Thus although successive ASEs are depicted in FIG. 5 as commencing the Sinus Preference Algorithm, it will be understood that either or both depicted instances of setting the first prolonged V-A interval to the physiologic V-A interval plus the MaxSPW, may be initiated by the lapse of the SCI.

Figure 9:
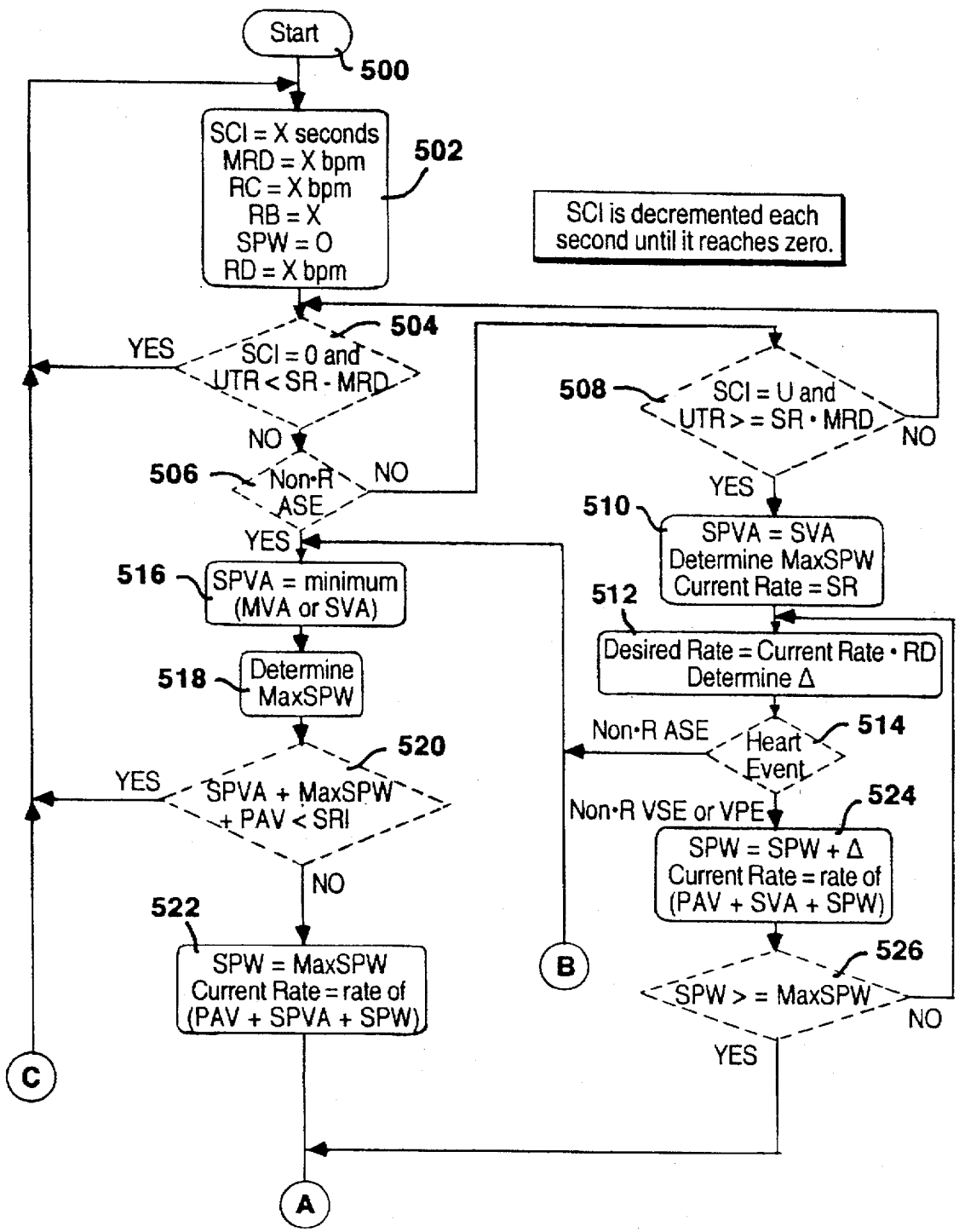
FIGS. 9 and 10 are a combined flowchart of the Sinus Preference Algorithm of the present invention that may be implemented in the pacemaker of FIGS. 1 and 7 in conjunction with the overall function of the flowchart of FIG. 8.
Figure 10:
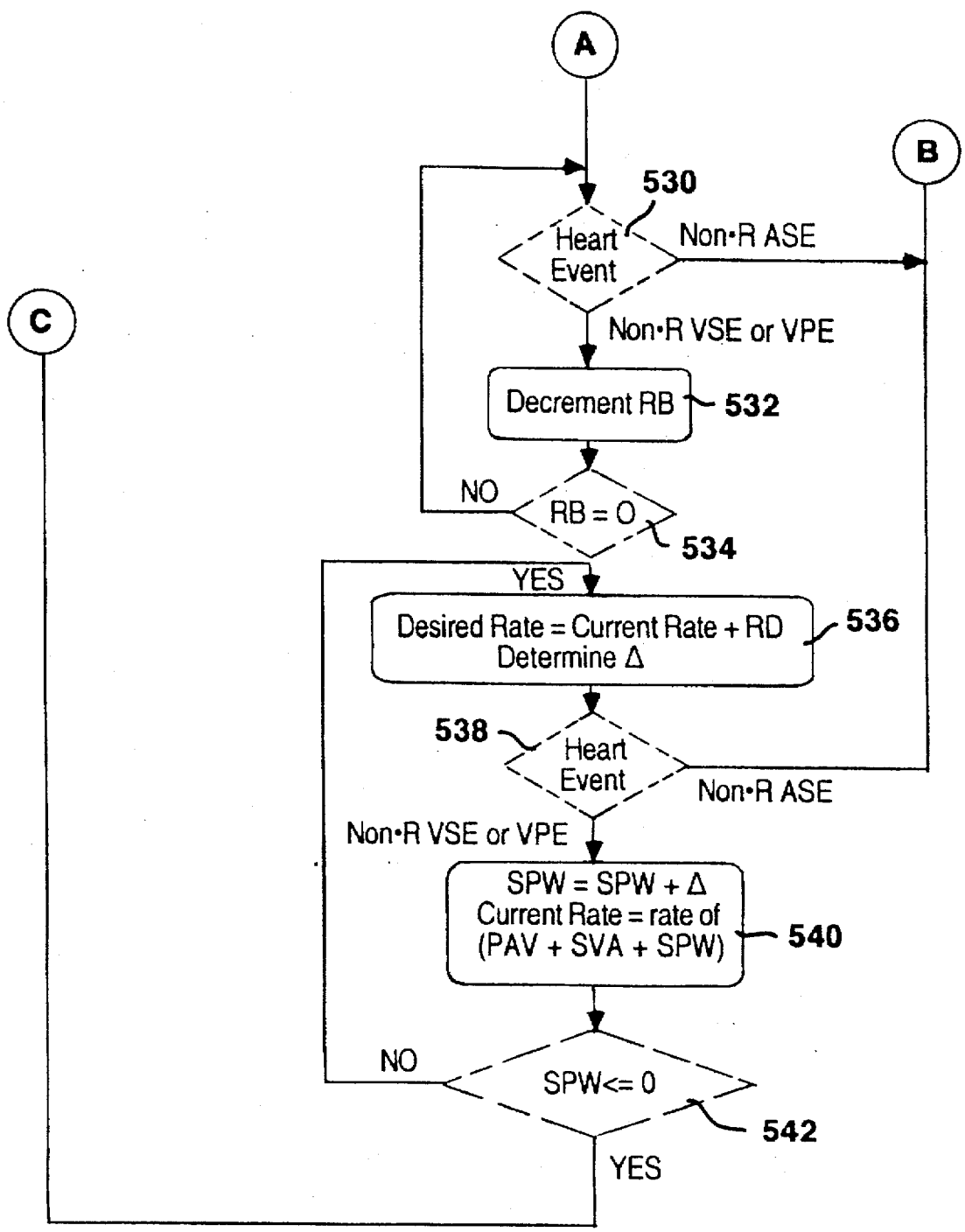

Turning now to the combined flowchart of FIGS. 9 and 10, it illustrates the steps of the Sinus Preference Algorithm of the present invention that may be implemented in the pacemaker of FIGS. 1 and 7 in conjunction with the overall function of the flowchart of FIG. 8. The flowchart of FIGS. 9 and 10 employ certain of the acronyms defined above and others including RC for SPW Rate Change, RB for Recovery Beats, UTR or Upper Tracking Rate which is related to the Upper Rate Limit, SR for sensor-derived pacing rate over a full A-A pacing cycle, Non-R for non-refractory, SPVA or Sinus Preference V-A interval (i.e., the prolonged V-A interval), RD for the incremental Rate Drop that is allowed at a given pacing rate, and SRI for Sensor Rate Interval, which is the sensor-derived A-A interval. Because of physician preference for interpreting pacemaker timing in terms of rate, and in order to scale interval changes to rate changes, the calculations and intervals defined in the flowchart of FIGS. 9 and 10 are at certain points done in terms of rate. In particular, the following relations of rate and interval are employed:

$$MaxSPW = interval\ of\ (rate\ of\ (SPVA+PAV)-MRD)-PAV-SPVA;$$

and $$delta\ (\Delta) = interval\ of\ Desired\ Rate - Interval\ of\ Current\ Rate$$

The SPW algorithm of FIGS. 9 and 10 is operational in the block 408 of FIG. 8 in response to a VPE or VSE in block 404 or 406 and the preceding measured V-A interval from block 424. The SPW algorithm is invoked on time out of the SCI or the ASE as follows.

At start block 500, the conditions are initialized in block 502 to reset the SCI, MRD, RC, RB, RD and SPW as shown in response to the setting of the SPW to zero in block 542 or other conditions of blocks 504 and 520. The SCI is programmable in seconds and commences to count down in seconds in this case. Each value for the parameters SCI, MRD, RD, RC, and RB is a separate physician programmable value within a possible range of values for each parameter and is indicated by "X" for simplicity.

At decision block 504, the SCI is monitored, and the relation of the UTR with SR and MRD is examined. If SCI is counted down to zero or timed out, and if UTR is less than the sensor-derived rate (SR) less the Maximum Rate Drop (MRD), then the starting conditions are reset in block 502. This insures that the algorithm is not followed if the UTR would be violated. If not, then the algorithm waits for the occurrence of a non-refractory ASE to occur during the SVA. As long as no Non-R ASE is detected, the state of the SCI counter/timer is continuously monitored. Either the time out of the SCI or a Non-R ASE can initiate the change to the SPVA under the Sinus Appropriate conditions illustrated in FIG. 4 and set forth in block 508.

First, if the SCI times out and the UTR is equal to or greater than the SR−MRD in block 508, then the SPVA is set to the SVA, the Current Rate is set to SR, and the MaxSPW is determined in accordance with the above formula in block 510. In block 512, the Desired Rate is determined as the Current Rate less the Rate Drop (RD), and the delta is determined by the above formula.

At the next Non-R ASE at block 514 (or at block 506 if UTR is greater than SR−MRD), the MVA value (derived in block 424 of FIG. 4) is compared to the SVA and the minimum is set to SPVA in block 516. The MaxSPW is determined from the above formula in block 518. If the sum of the SPVA, MaxSPW and PAV is less than SRI as found in block 520, then the Sinus Rate exceeds the sensor rate by more than the MRD, and the start values are reset to the programmed values "X" in block 502.

If the Sinus Rate is within the MRD of the sensor rate, then in block 522, the SPW is set to MaxSPW. The current pacing rate is determined to be equal to the rate corresponding inversely to the sum of the PAV and SPVA and SPW intervals, and the algorithm continues in FIG. 10.

Returning to block 514, if, instead, a Non-R VSE is detected or a VPE occurs, then the steps of blocks 524-526 are followed. In block 524, the next SPW is set to the current SPW plus delta, and the current rate is set to the rate corresponding inversely to the sum of the PAV and SPVA and SPW intervals. The next SPW is compared to MaxSPW in block 526, and, if equal to or greater, then the algorithm continues in FIG. 10. If less, then the algorithm loops back to block 512. In this fashion, when the next SPW is equal to MaxSPW, from either block 522 or 526, the algorithm continues in FIG. 10.

Turning to FIG. 10, the sense amplifiers are monitored in block 530. If a Non-R ASE is detected, then the SPVA for the next succeeding pacing cycle is again calculated in blocks 516 to 522. If a Non-R VSE is detected, then the RB number is decremented in block 532. When the RB count is decremented to zero as found in block 534, the Desired Rate of the next pacing cycle is set to the Current Rate plus RD in block 536, and delta is determined in block 536. The next sensed depolarization of the atrium in block 538 also causes the recalculation of the SPVA in blocks 516-522.

If a further Non-R VSE is sensed or a VPE occurs in block 538, then the SPW is incremented again with delta, and the current rate is set to the inverse of the sum of PAV and SVA and SPW for the next pacing cycle in block 540. This continues as long as the SPW is greater than zero. When SPW equals zero, the algorithm is reset at block 502 to the initial programmed operating conditions. Pacing at the sensor-derived pacing rate is re-commenced until the timeout of SCI or the sensing of a non-refractory ASE.

Variations and modifications to the present invention may be possible given the above disclosure. Although the present invention is described in conjunction with a microprocessor-based architecture, it will be understood that it could be implemented in other technology such as digital logic-based, custom integrated circuit (IC) architecture, if desired. For example, the present invention is not limited to any particular pacing mode, and can function with prior art modes such as DDDR, AAIR, VVIR and DDIR. For example, the specific modes of operation in establishing the prolonged escape interval beyond the sensor derived escape interval in response to a natural depolarization or a periodic check interval and then gradually decrementing the prolonged escape interval until the sensor derived escape interval is restored may be practiced in single chamber rate responsive pacemakers or one chamber of a dual chamber rate responsive pacemaker. It will also be understood that the present invention may be implemented in dual-chamber pacemakers, cardioverters, defibrillators and the like. However, all such variations and modifications are intended to be within the scope of the invention claimed by this letters patent.

We claim:

1. A rate-responsive pacemaker for pacing a patient's heart at a pacing rate comprising:

means for generating pacing pulses and applying the pulses to a chamber of a patient's heart;

means for sensing depolarization's of the heart chamber;

means for determining the physiologic demand on the patient's heart;

Means for defining physiologic escape intervals as a function of the physiologic demand on the patient's heart which establish a physiologic pacing rate;

means for adding incremental intervals to a predetermined number of physiologic escape intervals to define prolonged sinus escape intervals which allow for sensing a slower sinus rate than the physiologic pacing rate;

means for triggering generation of a pacing pulse on expiration of prolonged escape interval; and means for gradually decrementing the duration of the incremental intervals over a series of the prolonged sinus escape intervals in response to failure to sense depolarization's of the heart chamber within the prolonged sinus escape intervals.

2. The pacemaker of claim 1 wherein said means for adding incremental intervals adds said incremented intervals in response to a trigger signal generated in response to sensing of a depolarization of the heart chamber.

3. The pacemaker of claim 2 further comprising means for periodically searching for a sinus rhythm slower than said physiologic rate of the heart chamber by periodically adding the incremental interval to the sensor-derived escape interval to determine if a depolarization will be sensed, and, if present, retaining the prolonged escape interval as long as the depolarization's are sensed in subsequent heart cycles.

4. The pacemaker of claim 3 further comprising:

means for timing an amount of elapsed time during the escape intervals until the sensing of a depolarization occurs in the escape interval representative said interval until sensing and means for adding the incremental interval to the measured escape interval rather than the sensor the sensor-derived escape interval, if the measured escape interval is less than the sensor-derived escape interval, in setting the succeeding prolonged escape interval.

5. The pacemaker of claim 4 further comprising:

means for adding a full incremental interval to a currently active escape interval in setting the succeeding prolonged escape interval when the depolarization is sensed in a preceding escape interval.

6. The pacemaker of claim 5 further comprising:

means for defining a maximum pacing rate drop; and means for comparing the prolonged escape interval to the sensor-derived escape interval and, when the difference between pacing rate at the sensor-derived interval exceeds said maximum rate drop, employing a rate drop smoothing means for gradually decremenating said prolonged escape interval over a series of succeeding pacing cycles to restore said sensor-derived escape interval.

* * * * *